United States Patent [19]

Stoulil et al.

[11] 4,063,893

[45] Dec. 20, 1977

[54] DYE STABILIZED TRISODIUM PHOSPHATE CLEANING SOLUTION

[76] Inventors: Arthur C. Stoulil; William G. Stoulil, both of 10348 La Canada Way, Sunland, Calif. 91040

[21] Appl. No.: 723,037

[22] Filed: Sept. 13, 1976

[51] Int. Cl.² ............................................. G01N 21/06
[52] U.S. Cl. .................................. 23/230 R; 73/104; 134/42; 252/109; 252/408; 252/135
[58] Field of Search ........................ 23/230 R, 230 L; 134/42; 252/109, 408, 135; 73/104

[56] References Cited

U.S. PATENT DOCUMENTS

| | | |
|---|---|---|
| 1,915,965 | 6/1933 | Williams ............................ 23/230 L |
| 3,618,374 | 11/1971 | Miller .................................... 73/104 |
| 3,647,705 | 3/1972 | Mlot-Fijalkowski .............. 73/104 X |

*Primary Examiner*—R.E. Serwin
*Attorney, Agent, or Firm*—Fulwider, Patton, Rieber, Lee & Utecht

[57] ABSTRACT

A novel dye stablized cleaning solution of trisodium phosphate and a method of cleaning with said solution is provided by the disclosure. The novelty of said solution and method consists of forming the solution with tap water filtered with an activated charcoal and admixing a specific color indicating dye therewith. The color imparted by said dye remains stable and will not fade or settle-out in said solution. The presence of the trisodium phosphate solution is thereby readily detectable.

12 Claims, No Drawings

DYE STABILIZED TRISODIUM PHOSPHATE CLEANING SOLUTION

BACKGROUND OF THE INVENTION

Solutions of trisodium phosphate (TSP) are very useful cleaning agents for kitchen ware such as coffee makers, urns, pots and pans, and the like. Such solutions, however, do not foam as do conventional solutions of soaps and detergents, but are colorless and have the general appearance of water. As a result, TSP solutions may be mistaken for water and may not be thoroughly rinsed from kitchen ware prior to the preparation of food and beverages. If such solutions are allowed to remain in the kitchen ware, it would adversely affect the taste of foods and beverages prepared therein and may cause gastric problems if ingested.

The use of a color indicating dye admixed with TSP solutions would make such solutions readily visable and detectable but it has been found that such dyes are not stable in TSP solutions but will fade or settle-out of solution.

Accordingly, it is an object of the present invention to provide an aqueous solution of TSP compatible with a color indicating dye which will not fade or settle-out when in solution.

SUMMARY OF THE INVENTION

It has been discovered that if certain color indicating dyes are admixed with TSP solutions, the color imparted by said dye remains stable and will not fade. Said dyes are selected from the group consisting of disulfonate copper phthalocyanine, Alizarine Sapphire, tetraethylrhodamine, or a mixture of approximate equal parts of Alizarine Cyanone Green G and Fast Wool Yellow. The aforesaid dyes are not entirely satisfactory because each one settles-out of solution after a period of time. It has further been discovered, however, that if said TSP solution is made from tap water having a conductance and filtered with an activated carbon, each of said dyes remain in solution without settling-out over indefinite periods of time, and continues to impart a color to the TSP solution which will not fade. This discovery with respect to the particular type of water to be used is surprising in view of the fact that other types of water, i.e., untreated tap water, deionized water, distilled water, and water treated by a combination phosphate and activated charcoal filter, failed to prevent each of said dyes from settling-out of the TSP solution. It is not understood why the water treated with an activated carbon should work whereas other forms of water have failed, but regardless of the theoretical explanation, each of the aforesaid dyes will not fade and will not settle-out of TSP solutions when prepared from tap water having a conductance and treated with an activated charcoal.

PREFERRED EMBODIMENT OF THE INVENTION

The TSP solutions of the present invention are prepared from anyone of the aforesaid dyes. Disulfonate copper phthalocyanine which produces a blue color to said solution, is also known as Direct Blue 86 CI74180 and is sold under the trade name Solantine Turquoise G, by Allied Chemical Corporation.

Alizarine Sapphire, which produces a turquoise color to said solution, is the trade name of Allied Chemical Corporation for the sodium salt of the condensation product of 1-amino-4-bromo-2-anthraquinone sulfonic acid and p-amino-N-methylacetanilide in the presence of copper salts and acid binding agents.

Tetraethylrodamine, which produces a pink color to said solution, is also known as Basic Violet 10 CI45170 and is sold under the trade name Rhodamine B by the DuPont Chemical Company.

Alizarine Cyanone Green G is the trade name of the Allied Chemical Company for Acid Green 25 which has a formula pursuant to CI61570. Fast Wool Yellow is the trade name of the Allied Chemical Company for Acid Yellow 34 which has a formula pursuant to CI18890. A mixture of approximate equal parts of CI61570 and CI18890 produces a green color to said solution.

Any amount of the dye that produces a visible color to the TSP solution may be used.

About 100 pounds of TSP per 100 gallons of water is preferred but any other concentration of TSP which yields satisfactory results as a cleaning agent may be used.

The particular tap water that was used and filtered with an activated charcoal filter was Los Angeles aqueduct water blended with well water. This tap water is reported to have a conductance of 575 K $\times 10^6$ or a parts per million mineral content of 575, a pH of 7.74, and contains the following components expressed in milligrams per liter:

dissolved calcium residue-356
total hardness (calcium carbonate)-189
calcium-55
magnesium-13
sodium-43
potassium-3.5
alkalinity (calcium carbonate)-150
sulfate-93
chloride-28
nitrate-70
silica-21
iron-0.03
boron-0.31; and
fluoride-0.44

The activated carbon used to filter said tap water is manufactured from coconut base by stream activation and has the following characteristics:

| | |
|---|---|
| Carbon tetrachloride activity (pursuant to U.S. Military Specification C-1760b) | will absorb $CCl_4$ in an amount equal to at least 20% of its weight |
| Density (pursuant to ASTM D 2854) | typical .58 ± .05 grams/milliliter |
| Ash content (pursuant to ASTM D 2866) | maximum 4.0% by weight |
| Hardness (pursuant to U.S. Military Specification C-17605B) | only about 3% by weight can be ground into a powder |
| Moisture as packed (pursuant to ASTM D 2867) | maximum 3.0% by weight |
| pH of Extract | typical 8.5 – 10.5 |
| Surface area | typical 600 square meters/gram |
| Pore volume | typical .30 – .40 milligrams/gram |
| Particle size (pursuant to ASTM D 2862) | |
| On 6 mesh | maximum 5% |
| 6 × 12 mesh | minimum 90% |
| Thru 12 mesh | maximum 5% |

This particular carbon is sold by Westates Carbon Company of Los Angeles, California under the grade designation CC-311. For the sake of convenience, this carbon is hereinafter referred to in the claims as CC-311 activated carbon. Seventy cubic inches of this carbon was used in a cartridge through which the tap water was run. The particular cartridge used by the inventor is manufactured by Omnipure Filter Company of Long Beach, California and is described in U.S. Pat. No. 3,266,628, which is in corporated by reference into this specification.

The water contemplated for use in the present invention should provide an electrical conductance. Water which does not demonstrate some electrical conductance is not contemplated for use in the present invention because it will produce a solution wherein the dye will settle-out over a relatively short period of time.

While the embodiment chosen herein for purposes of the disclosure is considered to be preferred, it is understood that the invention is not limited thereto but comprehends any and all modifications, variations or changes thereto with fall within the spirit and scope of the invention.

We claim:

1. A method of detecting the presence of aqueous cleaning solutions of trisodium phosphate in kitchen ware comprising the steps of forming said solution with tap water having an electrical conductance and filtered with activated charcoal, and admixing a color indicating dye in said solution whereby the color imparted by said dye will not fade or settle-out of solution, said dye selected from the group consisting of:
    a. disulfonate copper phthalocyanine,
    b. Alizarine Sapphire,
    c. tetraethylrhodamine, or
    d. a mixture of approximately equal parts of Alizarine Cyanone Green G and Fast Wool Yellow.

2. A method as set forth in claim 1 wherein said activated carbon is CC-311 activated carbon.

3. A method as set forth in claim 1 wherein said dye is disulfonate copper phthalocyanine.

4. A method as set forth in claim 1 wherein said dye is Alizarine Sapphire.

5. A method as set forth in claim 1 wherein said dye is tetraethylrhodamine.

6. A method as set forth in claim 1 wherein said dye is a mixture of approximately equal parts of Alizarine Cyanone Green G and Fast Wool Yellow.

7. An aqeuous cleaning solution of trisodium phosphate formed with tap water having an electrical conductance and filtered with an activated charcoal, and having a color indicating dye whereby the color imparted by said dye will not fade and will not settle-out of said solution so that the presence of said trisodium phosphate solution is readily detectable, said dye selected from the group consisting of:
    a. disulfonate copper phthalocyanine,
    b. Alizarine Sapphire,
    c. tetraethylrhodamine, or
    d. a mixture of approximately equal parts of Alizarine Cyanone Green G and Fast Wool Yellow.

8. An aqueous cleaning solution of trisodium phosphate as set forth in claim 7 wherein said tap water is filtered with CC-311 activated carbon.

9. An aqueous cleaning solution of trisodium phosphate as set forth in claim 7 wherein said dye is a disulfonate copper phthalocyanine.

10. An aqueous cleaning solution of trisodium phosphate as set forth in claim 7 wherein said dye is a Alizarine Sapphire.

11. An aqueous cleaning solution of trisodium phosphate as set forth in claim 7 wherein said dye is a tetraethylrhodamine.

12. An aqueous cleaning solution of trisodium phosphate as set forth in claim 7 wherein said dye is a mixture of approximately equal parts of Alizarine Cyanone Green G and Fast Wool Yellow.

* * * * *

UNITED STATES PATENT AND TRADEMARK OFFICE
CERTIFICATE OF CORRECTION

PATENT NO. : 4,063,893
DATED : December 20, 1977
INVENTOR(S) : Arthur C. Stoulil and William G. Stoulil It is certified that error appears in the above-identified patent and that said Letters Patent are hereby corrected as shown below:

Column 1, line 19, "visable" should be -- visible --

Column 1, line 41, "remain" should be -- remains --

Column 1, line 61, "anyone" should be -- any one --

Column 2, line 44, "stream" should be -- steam --

Column 3, line 10, "in corporated" should be -- incorporated --

Signed and Sealed this

First Day of August 1978

[SEAL]

Attest:

RUTH C. MASON
*Attesting Officer*

DONALD W. BANNER
*Commissioner of Patents and Trademarks*